United States Patent [19]
King

[11] Patent Number: 5,814,092
[45] Date of Patent: Sep. 29, 1998

[54] NEURAL STIMULATION TECHNIQUES WITH FEEDBACK

[75] Inventor: Gary William King, Fridley, Minn.

[73] Assignee: Medtronic Inc., Minneapolis, Minn.

[21] Appl. No.: 853,306

[22] Filed: May 8, 1997

Related U.S. Application Data

[63] Continuation of Ser. No. 628,020, Apr. 4, 1996, Pat. No. 5,702,429.

[51] Int. Cl.[6] ............................................. A61N 1/08
[52] U.S. Cl. ................................... 607/46; 607/62
[58] Field of Search .................... 600/545, 546, 600/547, 554; 607/46, 62

[56] References Cited

U.S. PATENT DOCUMENTS

| | | |
|---|---|---|
| 3,850,161 | 11/1974 | Liss . |
| 4,524,774 | 6/1985 | Hildebrandt . |
| 4,543,955 | 10/1985 | Schroeppel . |
| 4,702,254 | 10/1987 | Zabara . |
| 4,750,499 | 6/1988 | Hoffer . |
| 4,867,164 | 9/1989 | Zabara . |
| 5,025,807 | 6/1991 | Zabara . |
| 5,081,990 | 1/1992 | Deletis .................................... 600/554 |
| 5,167,229 | 12/1992 | Peckham et al. . |
| 5,284,154 | 2/1994 | Raymond et al. ....................... 600/554 |
| 5,293,879 | 3/1994 | Vonk et al. . |
| 5,507,788 | 4/1996 | Lieber ........................................ 607/48 |

FOREIGN PATENT DOCUMENTS

| | | | |
|---|---|---|---|
| 0236513 | 9/1987 | European Pat. Off. .......... | A61B 5/04 |
| 93/20751 | 10/1993 | WIPO ............................... | A61B 5/05 |

OTHER PUBLICATIONS

Heinrich Bantli, Ph.D., et al., "Supraspinal Interactions Resulting from Experimental Dorsal Column Stimulation", *Journal of Neurosurgery*, vol. 42, Mar., 1975, pp. 296–300.

Michael Chichton, "The Terminal Man", *First Ballatine Books Edition*, Jan., 1988, pp. 16–27.

*Primary Examiner*—William E. Kamm
*Assistant Examiner*—George R. Evanisko
*Attorney, Agent, or Firm*—Banner & Witcoff Ltd

[57] ABSTRACT

Feedback is used to control a pulse generator that stimulates electrically excitable tissue. An implanted lead includes stimulation electrode(s) that are spaced from recording electrode(s). The compound action potential received by the recording electrode(s) is processed and integrated over a time window in order to control the amplitude of the pulse generator to maintain more uniform effect from the stimulation.

8 Claims, 5 Drawing Sheets

NEURAL STIMULATION TECHNIQUES WITH FEEDBACK

This is a continuation of application Ser. No. 08/628,020, filed Apr. 4, 1996, now U.S. Pat. No. 5,702,429.

BACKGROUND OF THE INVENTION

1. Field of the Invention

This invention relates to implantable techniques for stimulating electrically excitable tissue, and more particularly relates to such techniques for improving the uniformity of the response to tissue stimulation.

2. Description of the Related Art

Stimulation of neural tissue to reduce pain is a known therapy. Conscious sensation from stimulation is called paresthesia. It is commonly believed that pain relief with stimulation is strongly correlated to the overlap of the area of paresthesia and the area of pain.

Frequently, electrodes are implanted adjacent the spinal cord in order to create the electrical stimulation of neural tissue which creates the paresthesia. In some patients with such an implant, the paresthesia changes dramatically when there is a change in body position, such as standing up from a reclining position. It is difficult if not impossible for the user to properly adjust the electrical stimulation to create an essentially constant or uniform paresthesia. Sometimes the patient will use a lower level of stimulation than optimal in order to avoid "shocks".

Currently available totally implantable electrical stimulation systems offer two amplitude levels of stimulation, and employ a magnet to jump between levels depending on perceived paresthesia. U.S. Pat. No. 5,031,618 (Mullett) describes a system to determine body orientation with respect to gravity, and jumps between levels automatically. Portable programmers are available to adjust amplitude or frequency of the electrical stimulation periodically. Radio frequency systems also allow changing of parameters deliberately. None of these systems is capable of maintaining a substantially constant or uniform degree of paresthesia, and hence, none achieves optimal pain reduction.

SUMMARY OF THE INVENTION

The invention is useful for automatically controlling the paresthesia resulting from electrical stimulation of electrically excitable tissue. In a preferred embodiment, a stimulation driver generates in response to a control signal a stimulation pulse having a predetermined pulse period and a predetermined amplitude. An implanted stimulation electrode delivers the pulse to produce action potentials in the tissue. A recording electrode is displaced from the stimulation electrode by a predetermined distance. The recording electrode receives the action potentials transmitted along the tissue. An amplifier generates a processing signal responsive to the action potentials received by the recording electrode. A controller adjusts the control signal in response to the processing signal.

The control signal is related to a predetermined property of the action potentials. For example, the action potentials may be integrated over a window of time in order to determine the activity level of the tissue that creates the best paresthesia. By adjusting the control signal in accordance with the predetermined property, the stimulation pulse is adjusted in order to provide a more nearly uniform paresthesia in the body part of interest.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
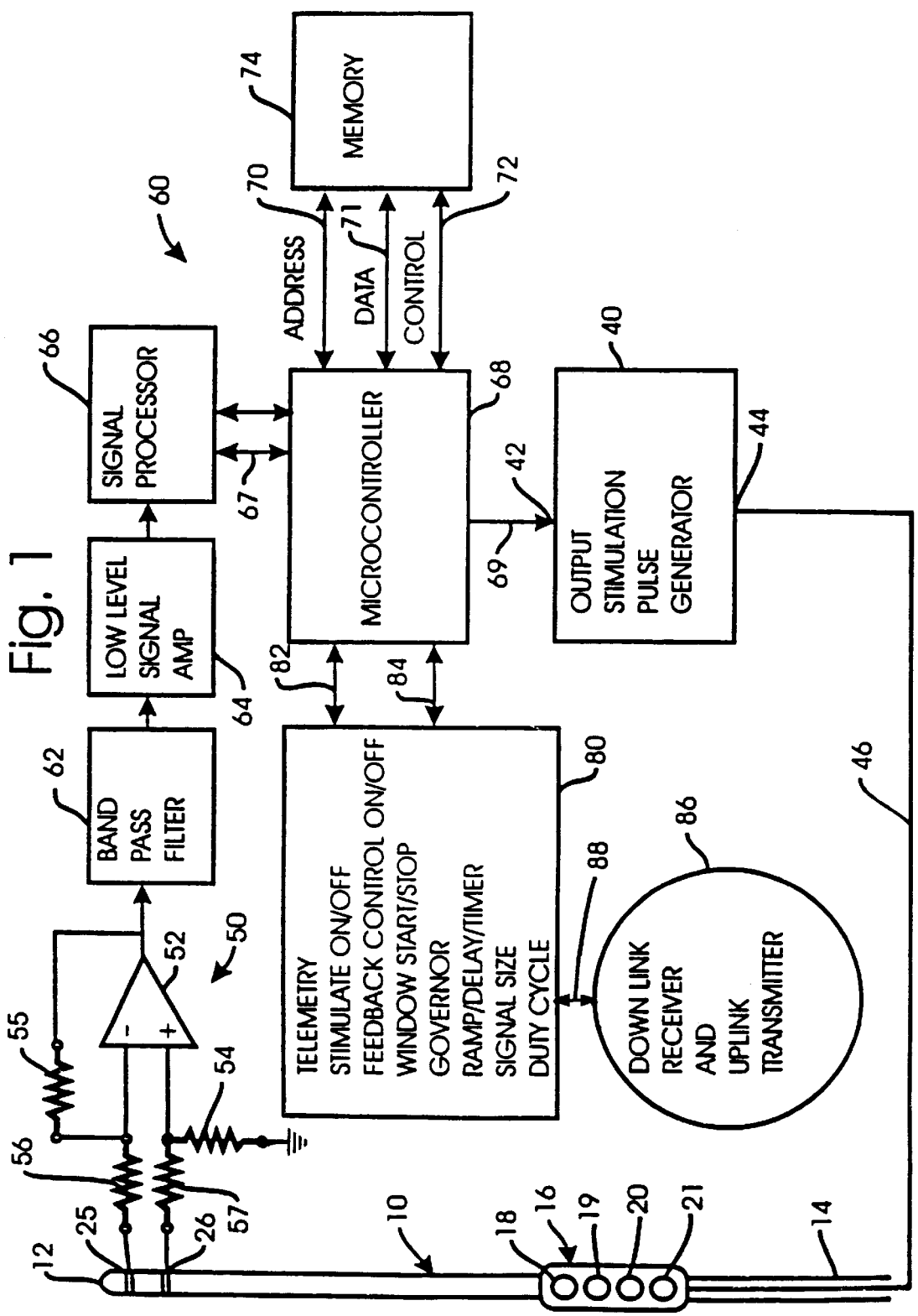
FIG. 1 is a schematic diagram of a preferred form of stimulation and recording lead made in accordance with the present invention, together with a preferred form of system for adjusting a stimulation pulse applied to the lead.

Referring to FIG. 1, a preferred form of stimulating and recording lead 10 made in accordance with the present invention includes a generally cylindrical distal end 12 and a generally cylindrical proximal end 14. Lead 10 also includes a flat paddle 16 that can be typically 8–12 mm wide, 1–2 mm thick and 40–50 mm long. Cylindrical portions 12 and 14 preferably have a diameter of about 1.25–1.50 mm. Cylindrical portions 12 and 14 may include a center stylet to add sufficient strength to facilitate the process of inserting lead 10, especially distal tip 12, into a position adjacent nerve fibers of a patient.

Paddle 16 includes stimulation electrodes 18–21 mounted on the surface of the paddle as shown. Stimulation electrodes 18–21 are each about 12 $mm^2$ and are fabricated from a platinum/iridium alloy. Each of the stimulation electrodes is connected to a separate lead wire collectively shown as a cable 46. Paddle 16 can take the form of the electrode lead sold by Medtronic, Inc. under the trademark "Resume II".

Lead 10 also supports recording electrodes 25 and 26 that are 1 $mm^2$ or less in surface area. They typically sense extracellular action potentials of about 1–100 microvolts. The distance between stimulation electrode 18 and recording electrode 26 preferably is 3–20 cm.

Stimulation electrodes 18–21 receive electrical pulses from an output stimulation pulse generator 40 having an input 42 which receives a control signal and an output 44 connected to four-wire cable 46. Generator 40 is well known in the art. Such pulse generators also are made by Medtronic, Inc. under the trademarks: Itrel II 7424, X-trel and Mattrix.

Still referring to FIG. 1, recording electrodes 25 and 26 are connected to a conventional differential amplifier 50 comprising an operational amplifier 52 and resistors 54–57 connected as shown. The conductors between electrodes 25 and 26 and resistors 57 and 56 preferably are located within lead 10, but recording electrodes can also be on a separate lead altogether.

The output of amplifier 50 is connected to a controller 60 basically comprising a band pass filter 62, a low level signal amplifier 64, a signal processor 66, a microcontroller 68, a memory 74, a telemetry unit 80 and a receiver/transmitter unit 86.

More specifically, signal processor 66 may take the form of a digital signal microprocessor, or, alternatively, an analog to digital converter. The output of signal processor 66 is conducted over a bus 67 to microcontroller 68. Microcontroller communicates with memory 74 over an address bus 70, a data bus 71 and a control bus 72. An output port of microcontroller 68 produces a control signal on an output bus 69. Microcontroller 68 communicates with telemetry unit 80 over buses 82 and 84. The telemetry unit communicates with receiver/transmitter unit 86 via a bus 88.

Figure 2:
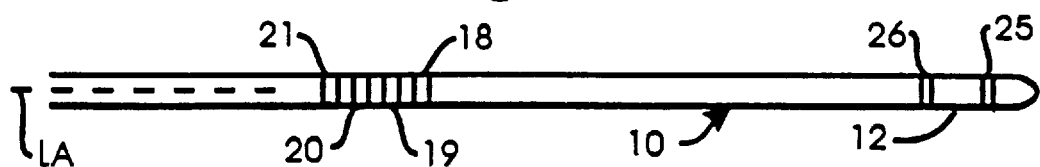
FIGS. 2–5 are various embodiments of the stimulation and recording lead made in accordance with the invention.

Alternative embodiments of lead 10 are shown in FIGS. 2–5. In FIG. 2, the lead takes the form of a cylinder in which end 12 extends in the cranial direction. Electrodes 18–21 are preferably about 3 mm long with a gap of about 6 mm between the electrodes. Lead 10 preferably has the same diameter as lead models 3487A or 3888 sold by Medtronic, Inc., i.e., about 1.25–1.50 mm.

In practice, lead 10 is positioned so that stimulating electrodes 18–21 are at the optimal sites adjacent electrically excitable tissue for control of conscious paresthesia into the painful area of a patient. Electrically excitable tissue includes: neural tissue intrinsic to the heart and other organs, a peripheral nerve, the spinal cord surface, the interior of the spinal cord, deep brain tissue, brain surface tissue, and neural ganglia. Although the specification describes the use of the invention adjacent the dorsal columns of the spinal cord or along peripheral nerves, the invention can be used to advantage adjacent any electrically excitable tissue. Recording electrodes 25 and 26 have the same medio/lateral position in the dorsal columns or are aligned with ascending axons from cells targeted for stimulation. For stimulation of the dorsal columns, recording electrodes 25 and 26 might be maneuvered to be slightly more medial than electrodes 18–21, since dorsal column fibers tend to drift medially as they ascend in the cranial direction. For peripheral nerve stimulation, both stimulating and recording electrodes are placed near the nerve of interest.

Figure 3:
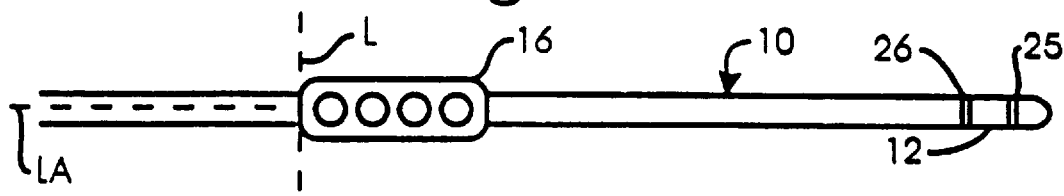

Referring to FIG. 3, lead 10 would be inserted in a cranial direction from the laminotomy site L with the aid of a temporary stylet. End 12 with recording electrodes 25 and 26 is advanced cranially.

Figure 4:
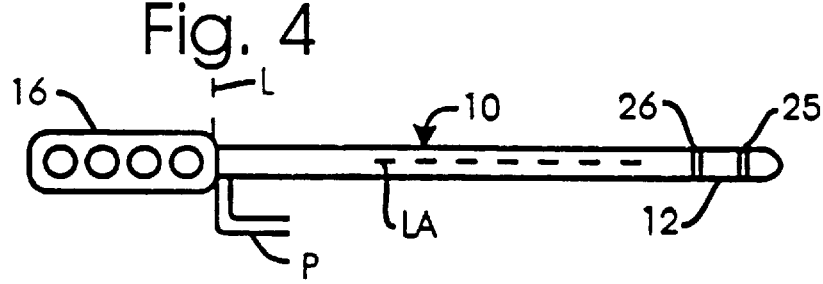

Referring to FIG. 4, paddle 16 is inserted caudally from the laminotomy site L with end 12 inserted cranially. The embodiment of FIG. 4 also includes a cylindrical proximal lead body P through which wires are connected to the stimulating electrodes and recording electrodes.

Figure 5:
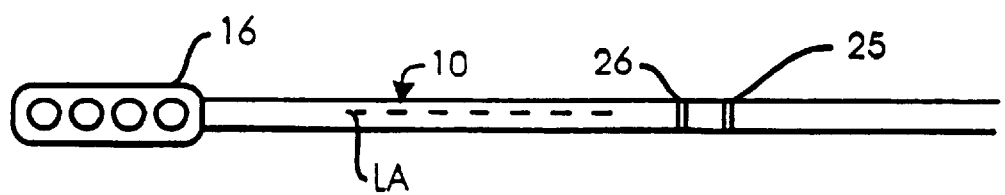

The embodiment of FIG. 5 requires that the recording electrodes 25 and 26 be located proximally along the lead and be positioned by suture close to the nerve being stimulated.

In all of the embodiments of FIGS. 2–5, electrodes 18–21, 25 and 26 are aligned with a longitudinal axis LA.

Figure 7:
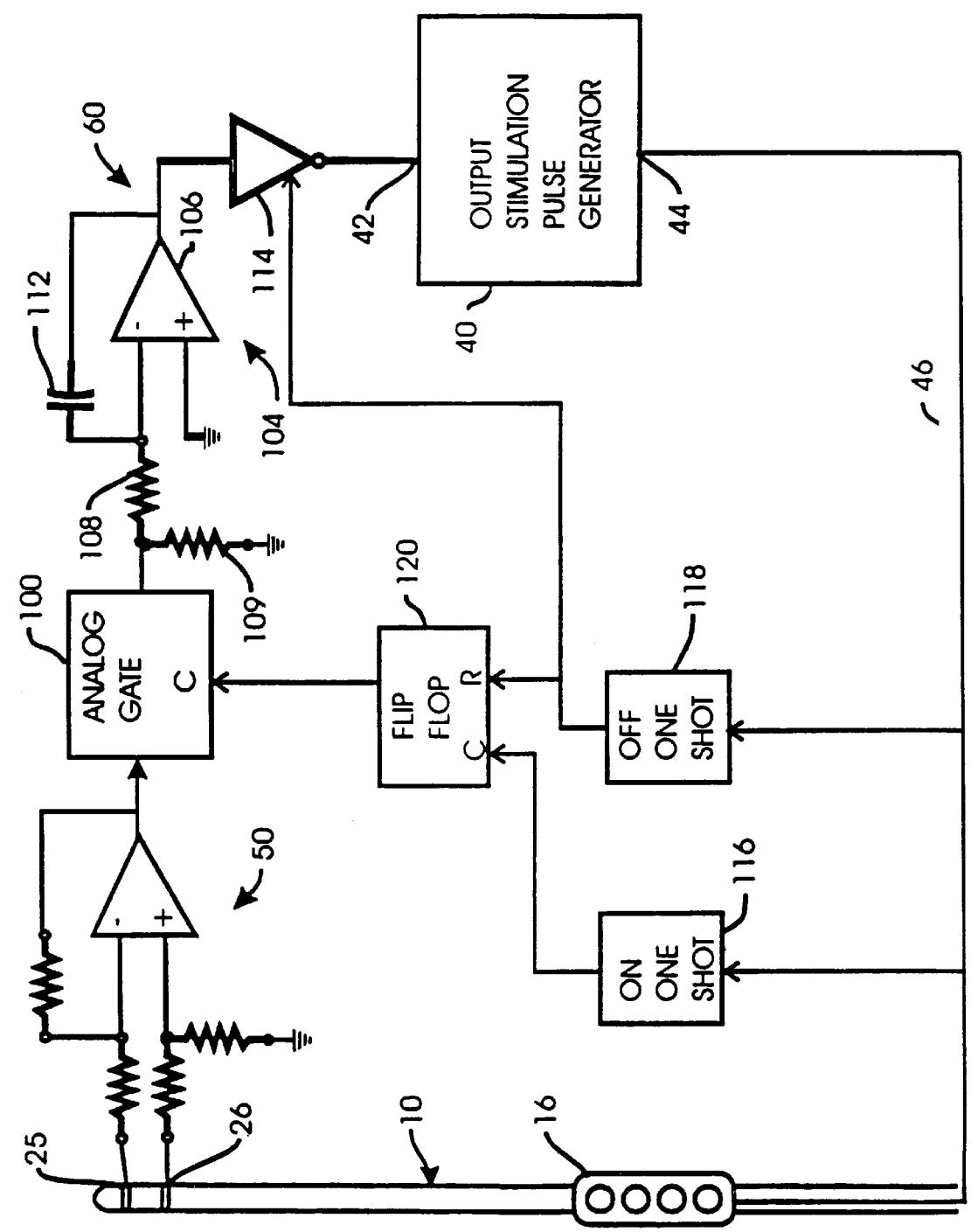
FIG. 7 is an electrical schematic diagram of an alternative form of circuitry for adjusting a stimulation pulse applied to the stimulation and recording lead.

Referring to FIG. 7, an alternative embodiment of controller 60 includes differential amplifier 50, a conventional analog gate 100, an integrator comprising an operational amplifier 106, resistors 108–109 and a capacitor 112 connected as shown, as well as a sample and hold circuit 114.

Output cable 46 is connected to an "on" one shot multivibrator 116, and an "off" one shot multivibrator 118. The outputs of one shots 116 and 118 are connected to the clock C and reset R inputs of a conventional flip flop 120. The output of flip flop 120 is connected to the clock terminal C of analog gate 100.

In order to use the preferred embodiment, the positions of stimulating electrodes 18–21 and recording electrodes 25–26 must be fine-tuned to obtain the correct paresthesia and extra-cellular recordings. Recordings of potentials evoked in the nerve fibers adjacent lead 10 are picked up at the recording sites and analyzed to see if there is sufficient potential received from large diameter afferents in the dorsal columns or peripheral nerve.

Figure 6:
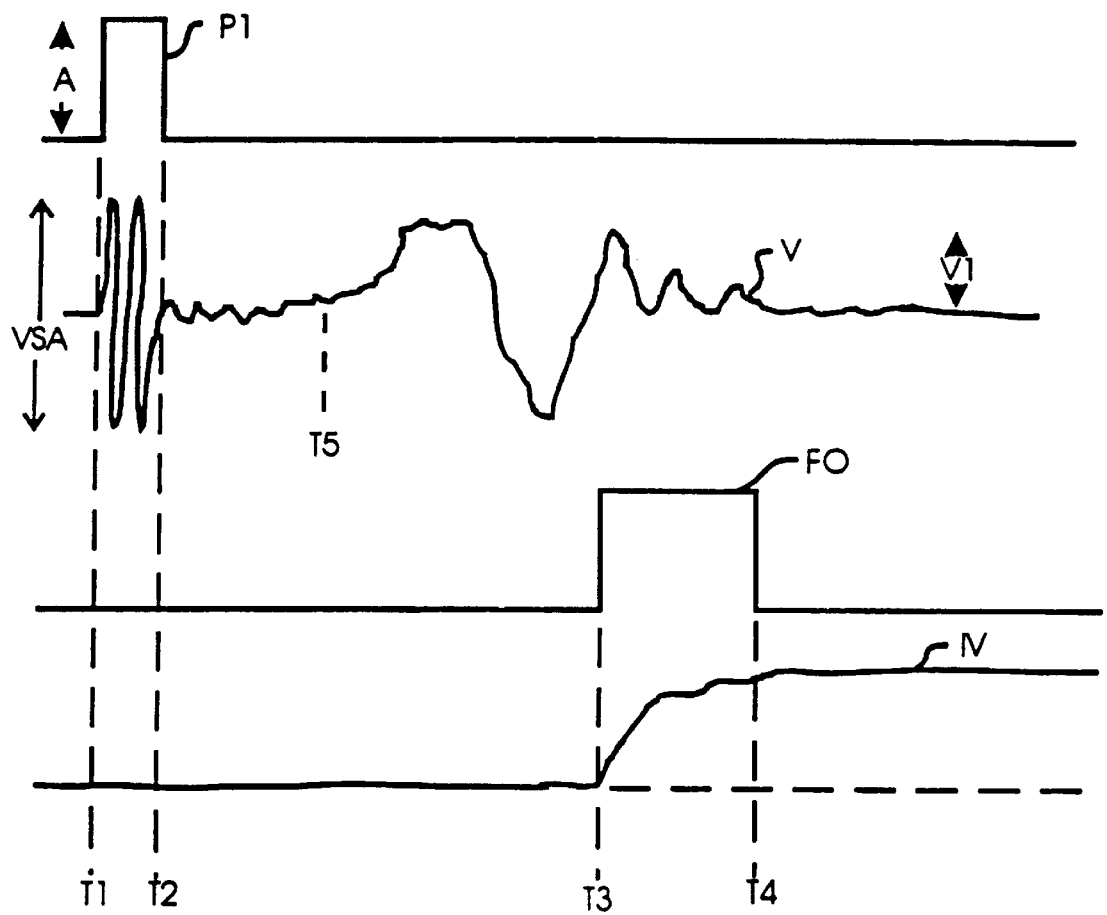
FIG. 6 illustrates wave forms generated by portions of the circuitry shown in FIG. 1.

The processing signal obtained from potentials received at recording electrodes 25 and 26 is integrated over a time window. Referring to FIG. 6, a pulse P1 produced by generator 40 begins at time T1 and ends at time T2. The time between T1 and T2 defines a pulse period, preferably about 210 microseconds. Pulse P1 has a predetermined amplitude A, typically about 4 volts. The repetition rate of the pulse P1 is typically about 80 Hz.

Pulse P1 produces in recording electrodes 25 or 26 a corresponding large voltage (stimulus artifact) having a value VSA>about 1 mV. Voltage V after time T2 corresponds to a compound action potential created by pulse P1 in nerve fibers, arriving at recording electrodes after at least a certain time, T5.

Referring to FIG. 7, "on" one shot 116 begins its timing at time T1 (FIG. 6) and clocks the C input of flip flop 120 at time T3 (FIG. 6). "Off" one shot 118 begins its timing at time T1 and energizes the reset input of flip flop 120 at time T4. As a result, the output of flip flop 120 creates a gating pulse F0 that causes analog gate 100 to conduct the compound action potential V to operational amplifier 104 from time T3 to T4. The values of one shots 116 and 118 are varied so that time T3 begins after the stimulus artifact from pulse P1 has stopped. The evoked potential V in the nerve fibers arrives at recording electrodes 25 and 26 via the nerve fibers the practitioner wishes to include, the ones contributing to pleasant paresthesia in the area of pain. In dorsal columns, typically these nerve fibers conduct action potentials from about 100 meters per second down to 40 meters per second, although velocities might be slower if fibers become thinner as they ascend in the dorsal columns. For example, if recording electrode 26 is located 10 cm from the most cranial stimulating electrode 18, the compound action potentials from the nerve fibers would arrive at 1.0 millisecond from the end of pulse P1 for fibers conducting at 100 meters per second and at 2.5 milliseconds for fibers conducting at 40 meters per second. So T3 should be adjustable to be 1–2.5 milliseconds or more after T2. For peripheral nerve stimulation, the fastest fibers may be efferent alpha-motor neurons, not efferent fibers carrying pleasant paresthesia. The window start T3 can be chosen to exclude antidromic motor neuron action potentials from the feedback signal.

Time T4 depends on two factors: the smallest diameter of nerve fiber (i.e., the nerve fiber conducting action potentials at the slowest conducting velocity) that contributes to pleasant paresthesia, and possible negative swings in the evoked compound action potential as it moves cranially. Typically, the time window from T3 to T4 might be about 1.5 milliseconds wide, or up to 5 or 10 milliseconds wide, or even longer (but always less than the repetition period of pulse P1). Sample and hold circuit 114 is gated at time T4 so that the value of signal IV (FIG. 6) at time T4 is stored and transmitted to input 42.

During the surgical operation, the practitioner must position the stimulating electrodes 18–21 optimally over electrically excitable tissue. Then and at any time later, any of the electrodes may be turned on or off or have its polarity adjusted to + or − to give paresthesia to optimally cover the area of pain. Closed loop feedback control would then be used to finally control amplitude of pulses.

Referring to FIG. 7, differential amplifier 50 is an advantageous feature of the preferred embodiment. By using a differential amplifier, the effect of the distorting voltages (such as noise from the stimulus artifact) unrelated to compound action potentials received by electrodes 25 and 26 are greatly reduced. Differential amplifier 50 creates a processing signal which is more accurately processed by integrator 104. The recording signal also may come from a single electrode.

The output of analog gate 100 is integrated from time T3 to time T4 in order to produce the control signal at conductor 42. The output of integrator 104 is shown by voltage IV in FIG. 6. By using an integrator from times T3 to T4, the control signal more accurately simulates the degree of paresthesia likely to be felt by the user. The resulting control signal on conductor 42 can be used to adjust the amplitude A or the width of pulse P1 (FIG. 6) in order to maintain the uniformity of the paresthesia. If the amplitude of control signal on conductor 42 diminishes, indicating loss of optimal parts of the compound action potential, the amplitude of pulse P1 is increased proportionately in order to maintain the paresthesia at the desired level. The control signal adjusts the output of generator 40 in order to maintain substantially the same value of integrated signal IV.

Alternative embodiments are possible. For example, to save battery power, the circuit shown in FIG. 7 could be arranged so that it is activated only for every tenth or twentieth voltage pulse P1. Either or both of the stimulating and recording electrodes may be subdural as well as epidural for spinal cord stimulation. Recording electrodes also could be placed near the dorsal column nuclei, in the thalamus, or over sensory brain cortical areas for either peripheral nerve stimulation or spinal cord stimulation, thereby sensing potentials in other neurons related to the paresthesia. In certain circumstances, for example, peripheral nerve stimulation, control of polarities and active electrodes might be done based on feedback signals from the recording electrodes.

Referring to FIG. 1, by using telemetry unit 80, controller 60 can be turned on or off in order to provide stimulation of nerve fibers adjacent lead 10. In addition, feedback control can be turned on or off. When feedback control is turned on, differential amplifier 50, band pass filter 62, amplifier 64, signal processor 66, microcontroller 68 and memory 74 are switched from an inactive to an active state. The window from time T3 to T4 (FIG. 6) also can be adjusted as previously explained. The telemetry unit also may permit the use of a governor which sets a maximum safe amplitude of pulse P1 to keep the maximum paresthesia comfortable. The maximum amplitude of pulse P1 is determined empirically with each patient. The telemetry unit also may provide a ramp/delay/timer feature which allows the automatic feedback controller to start or stop gradually, or to start or stop at a selected time. Other stimulation features used at present (duty cycle, modulation) may also still be available with or without feedback amplitude control.

Telemetry unit 80 also can provide the ability to adjust the signal size automatically, when the stimulation system is first turned on, by gradually increasing the amplitude of pulses until a prior stored value of paresthesia feedback signal is produced. Memory unit 74 can store prior parameters of stimulation, polarities, or size of recorded paresthesia signal.

Microcontroller 68 can be programmed to perform the foregoing functions described in connection with telemetry unit 80 by those skilled in the art.

Figure 8:
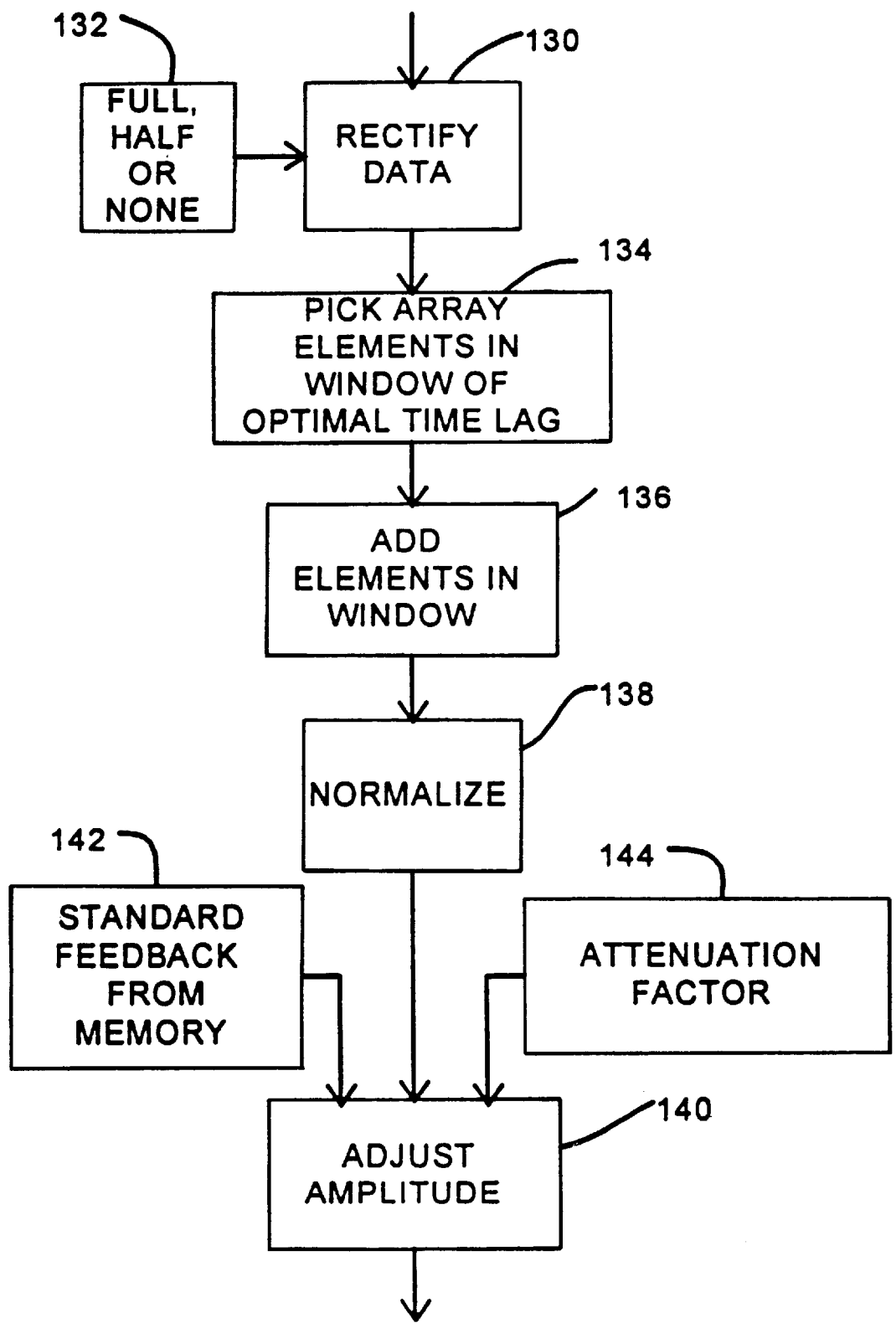
FIG. 8 is a flow diagram of an algorithm executed by the system shown in FIG. 1.

Referring to FIGS. 1 and 8, microcontroller 68 can be programmed to execute an algorithm which enables feedback from action potentials at recording electrodes 25 and 26 to adjust the amplitude of stimulation pulses produced by generator 40 at output terminal 44. The algorithm begins at step 130 by rectifying digital data stored in memory 74 by microcontroller 68 based on digital values of an analog voltage created by signal processor 66. The data represents the voltage V shown in FIG. 6 in digital form. In step 134, the algorithm picks a subset of data elements in a window corresponding to optimal time lag from time T3 to time T4 (FIG. 6). The values of the digital voltage elements $X_i$ from time T3 to T4 are added in step 136 ($\Sigma X_i$ for K values) and are normalized in step 138 (by 1/K) to give a normalized signal $\bar{x}$. In step 140, the amplitude of the pulses produced by generator 40 is adjusted by scaling the previous amplitude parameter. Output circuits in microcontroller 68 generate a signal transmitted to input 42 of pulse generator 40 (FIG. 1) to adjust the amplitude of the pulses transmitted from output 44 according to the scaling factor.

One example of scaling is to multiply the previous amplitude parameter by the factor: $\exp[\alpha(1-\bar{x}/x_m)]$. In the foregoing expression, alpha ($\alpha$) is an attenuation factor and $x_m$ is a standard feedback value obtained from memory 74. The attenuation factor and the exponential factor are used to make changes in the amplitude of the output pulses from generator 40 more gradual than they would be if the amplitude were changed simply according to the ratio of the normalized value $\bar{x}$ to the standard feedback value from memory $x_m$. The attenuation factor can vary from about 0.05 to 1.0.

Step 132 represents an input parameter telling step 130 whether to execute full rectification, half rectification or no rectification. The standard feedback value from memory $x_m$ may be the last recorded normalized feedback signal which was stored in memory 74 before feedback control was last discontinued or may be the first normalized feedback signal once feedback control is initiated.

If lead 10 shifts position somewhat, or if the paresthesia sensation changes over time, practitioners will be able to tune the integration window by altering the delay periods of one shots 116 and 118 (FIG. 7) which are adjustable or by changing the window start/stop time (T3, T4) with telemetry unit 80 (FIG. 1).

Those skilled in the art will recognize that the preferred embodiments may be altered or amended without departing from the true spirit and scope of the invention as defined in the accompanying claims. For example, the algorithm shown in FIG. 8 can be used to control pulse amplitude (either current or voltage) or pulse width of the pulses produced by generator 40.

I claim:

1. A method of automatically adjusting action potentials in a nerve tissue of a living organism by electrical stimulation of said nerve tissue, said method comprising the steps of:

generating in response to a control signal a stimulation pulse having a pulse period and an amplitude;

applying said stimulation pulse at a first site on said nerve tissue to cause said action potentials in said nerve tissue, wherein at least one of said pulse period and said amplitude determines said action potentials generated in said nerve tissue;

receiving said action potentials transmitted by said nerve tissue at a recording locus of said nerve tissue, said recording locus being separated from said first site by a predetermined continuous portion of said nerve tissue;

generating a processing signal responsive to said action potentials received at said recording locus of said nerve tissue;

generating said control signal in response to said processing signal; and reducing pain experienced by said living organism uniformly with time by adjusting at least one of said pulse period and said amplitude from said control signal to maintain said action potentials generated in said nerve tissue at substantially a predetermined action potential level.

2. A method, as claimed in claim 1, wherein said recording locus comprises a first recording site and a second recording site.

3. A method, as claimed in claim 2, wherein said step of generating said processing signal includes determining a difference signal corresponding to a difference between the action potentials received at said first and second recording sites.

4. A method, as claimed in claim 1, wherein said step of generating said control signal comprises the step of varying said amplitude of said stimulation pulse inversely relative to said processing signal.

5. A method, as claimed in claim 1, wherein said step of generating said control signal comprises the step of limiting the amplitude of said stimulation pulse to not exceed a maximum amplitude.

6. A method for reducing, uniformly with time, pain experienced by a living organism having nerve tissue, said method including the steps of:

A. applying a stimulation pulse at a first locus of said nerve tissue to affect an action potential generated in said nerve tissue, wherein said stimulation pulse has a pulse period and an amplitude, and wherein at least one of said pulse period and said amplitude of said stimulation pulse affects said action potential;

B. measuring said action potential transmitted through said nerve tissue at a second locus of said nerve tissue, said second locus being separated from said first locus by a predetermined continuous portion of said nerve tissue; and C. determining said pulse period and said amplitude of said stimulation pulse in response to said action potential measured at said second locus of said nerve tissue such that said action potential transmitted through said nerve tissue is maintained at a predetermined action potential level to reduce pain experienced by said living organism, uniformly with time.

7. A method, as claimed in claim 6, wherein said step C includes the step of integrating said action potential measured at said second locus in adjusting said stimulation pulse.

8. A method, as claimed in claim 6, wherein step C of determining said amplitude of said stimulation pulse includes a step of limiting said amplitude of said stimulation pulse to not exceed a maximum amplitude.

\* \* \* \* \*